United States Patent
Mason

(10) Patent No.: US 7,851,748 B2
(45) Date of Patent: Dec. 14, 2010

(54) SYNCHRONOUS DATA ACQUISITION FOR MULTI-DIMENSIONAL ORTHOGONAL LIQUID SEPARATION SYSTEM

(75) Inventor: Michael Mason, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 935 days.

(21) Appl. No.: 11/690,212

(22) Filed: Mar. 23, 2007

(65) Prior Publication Data

US 2007/0231207 A1    Oct. 4, 2007

Related U.S. Application Data

(60) Provisional application No. 60/787,262, filed on Mar. 30, 2006.

(51) Int. Cl.
H01J 49/00 (2006.01)
(52) U.S. Cl. .................. 250/288; 250/281; 250/282; 250/287; 210/656; 210/659
(58) Field of Classification Search ................ 250/281, 250/282, 287, 288; 210/656, 659
See application file for complete search history.

(56) References Cited

U.S. PATENT DOCUMENTS

| | | | |
|---|---|---|---|
| 5,135,549 A | 8/1992 | Phillips et al. | |
| 6,503,399 B2 | 1/2003 | Ono et al. | |
| 7,107,818 B2 * | 9/2006 | Zilioli et al. | 73/23.41 |

* cited by examiner

Primary Examiner—Jack I Berman
Assistant Examiner—Michael Maskell
(74) Attorney, Agent, or Firm—Price, Heneveld, Cooper, DeWitt & Litton, LLP

(57) ABSTRACT

A circuit synchronizes the actuation of multi-dimensional separating valves with a system clock also coupled to a data acquisition circuit such that signals from a detector are synchronized and no signal information is lost. The system comprises an acquisition clock coupled to a data acquisition logic system and to a modulator valve control. The modulator valve control is, in turn, coupled to a multi-dimensional separation technique valve unit for controlling the valves for introduction of the eluant from a first separation column to a second, faster column in synchronism with acquisition of data by a detector.

20 Claims, 5 Drawing Sheets

SYNCHRONOUS DATA ACQUISITION FOR MULTI-DIMENSIONAL ORTHOGONAL LIQUID SEPARATION SYSTEM

CROSS-REFERENCE TO RELATED APPLICATIONS

This application claims priority under 35 U.S.C. §119(e) on U.S. Provisional Application No. 60/787,262 entitled SYNCHRONOUS DATA ACQUISITION FOR MULTI-DIMENSIONAL ORTHOGONAL LIQUID SEPARATION SYSTEM, filed on Mar. 30, 2006, by Michael Mason, the entire disclosure of which is incorporated herein by reference.

BACKGROUND OF THE INVENTION

The present invention relates to an electrical control circuit for synchronously acquiring data in a multi-dimensional orthogonal liquid separation system.

When separating the constituent elements of a liquid sample utilizing a multi-dimensional separation technique, typically through chromatographic columns and control valves, it has been difficult to accurately equate the acquisition of data with the detected signals for individual molecules. This leads to some loss of signal information, resulting in lower than desired signal-to-noise ratios. Any timing slips between the modulator, which provides relatively narrow peaks, and the data acquisition system results in an error in acquired data.

SUMMARY OF THE INVENTION

In order to overcome the deficiencies of the prior art, the system of the present invention synchronizes the actuation of multi-dimensional separating valves with a system clock also coupled to the data acquisition system such that signals from the detector are precisely synchronized and no signal information is lost. The system of the present invention, therefore, comprises an acquisition clock coupled to a data acquisition logic system and to a modulator valve control. The modulator valve control is, in turn, coupled to a multi-dimensional separation technique valve unit for controlling the valves for introduction of the eluant from a first separation column to a second, faster column in synchronism with acquisition of data by a detector circuit.

The detector circuit will typically include a multiplier detector coupled to a time-of-flight mass spectrometer (TOF/MS), and the pulsed liquid samples are ionized by an ionization source before introduction into the TOF/MS. The data acquisition system, single dimensional separation system, modulator, and TOF/MS are operated under the control of a personal computer, including a microprocessor, memory and interface circuits.

By synchronizing the data acquisition system and the multi-dimensional separation valves using a common system clock, the data received from the detector is synchronized with the separated peaks improving the accuracy of the system. These and other features, objects and advantages of the present invention will become apparent upon reading the following description thereof together with reference to the accompanying drawings.

DETAILED DESCRIPTION OF THE PREFERRED EMBODIMENT

Figure 1:
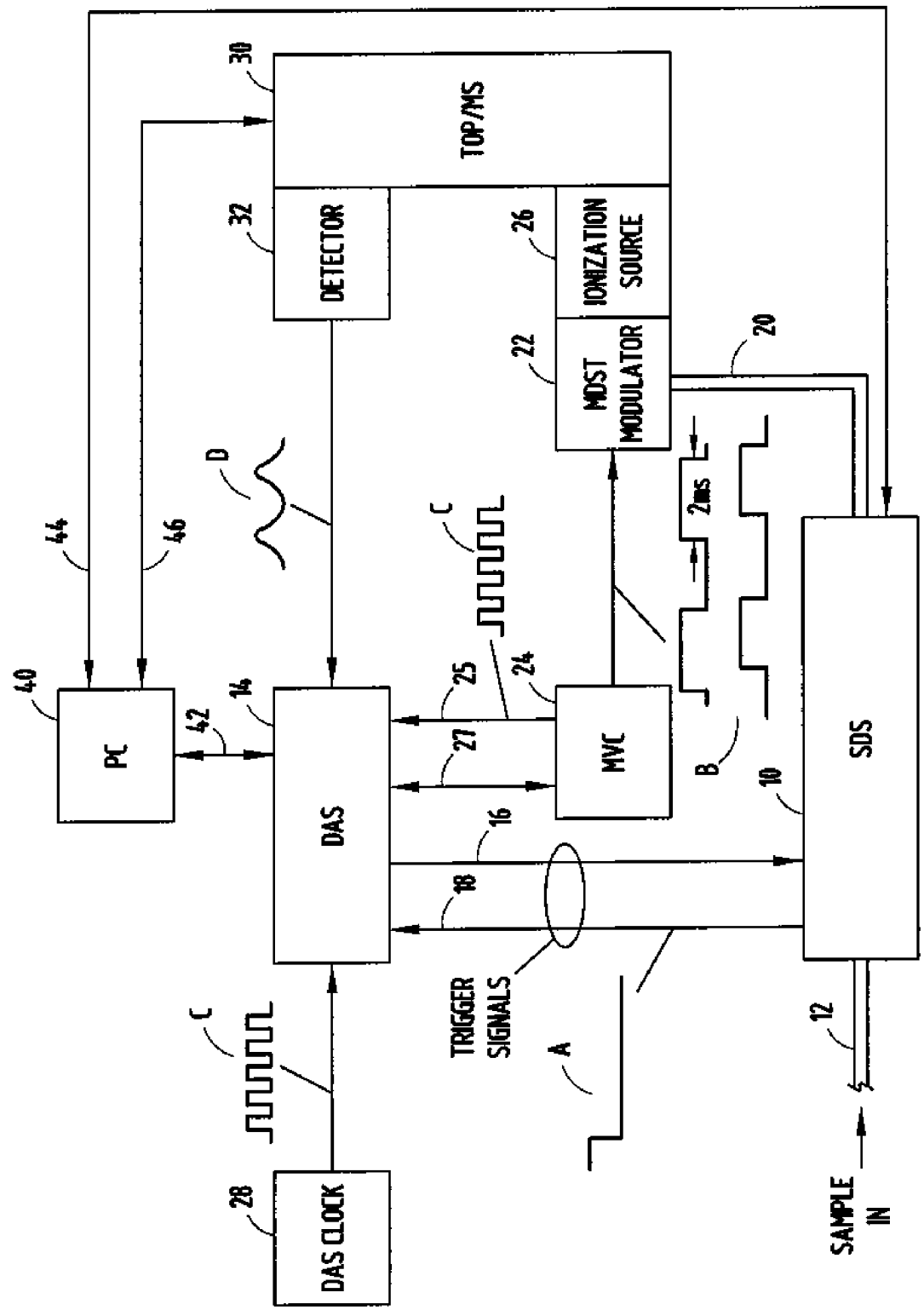
FIG. 1 is a block sample flow diagram and block electrical circuit diagram of the system of the present invention.

In FIG. 1, a liquid sample is introduced into a single dimension separation (SDS) unit 10 by conventional manners through an inlet 12. The SDS unit 10 receives operating parameters from computer 40 through a communication link 44 coupling a personal computer 40 to a unit 10. Computer 40 includes the customary microprocessor, RAM memory, hard disk storage, and Ethernet communication interface circuits. The SDS 10 also receives trigger signals (A in FIG. 1) from a data acquisition logic circuit 14 through two-way signal paths 16 and 18 to initiate the introduction of a liquid sample being analyzed. SDS 10 may be a commercial unit available from Agilent or Waters and includes a chromatographic column to provide separated liquid samples to an outlet 20, which is coupled to multi-dimensional separation technique and modulator unit 22. Unit 22 comprises electrically actuated valves which selectively and sequentially introduce the spaced liquid samples from input SDS 10 to a faster separating chromatographic column in unit 22. The second separation column may also include a commercially available chromatographic column, such as from Agilent.

The multi-dimensional separation unit (MDST) modulator 22 is controlled by a modulator valve control (MVC) 24, which provides electrical control output signals shown by waveform diagram B in the form of valve control square wave signals which are approximately 2 milliseconds in duration and which are offset to provide separation of the eluants from conduit 20. Conduit 20 includes a sample loop for suitably delaying the introduction of samples SDS 10 into the modulator 22. The first separation in SDS 10 may take anywhere from 15 minutes to 2 hours to complete the separation, depending upon the sample material and solvents used. The separated eluant peaks from SDS 10 are, in effect, stored and delayed in loop 20 and introduced through synchronously controlled valves into the second dimension separating column in modulator unit 22. The column in unit 22 is significantly faster in further separating molecular components contained in an eluant peak from SDS 10. The second dimension eluant peaks are then coupled to an ionization source 26 in fluid communication with the modulator 22. Clock pulses C from a data acquisition system clock 28 are coupled to a data acquisition logic circuit 14 and are also applied to the modulator valve control circuit 24 by electrical conductor 25 to synchronize the valve control signals B with the clock pulses C. Two-way communication link 27 couples the modulator valve control circuit 24 to the data acquisition circuit 14 for providing the synchronized output signals B from circuit 24.

The pulsed eluant samples from modulator 22 are ionized and coupled to a TOF/MS 30, which separates the now ionized samples based on their mass/charge ratio. The ionized samples strike the detector 32, which provides analog signal outputs shown by waveform D to the input of the data acquisition system 14. These peaks occur in timed relationship to clock pulses C and are read in synchronization with the data acquisition logic circuit 14 operation such that the data is accurately obtained.

The personal computer (PC) 40 is coupled by a high speed Ethernet link 42 to the data acquisition logic circuit 14 and similar link 46 to the TOF/MS 30, The PC 40 is programmed in a conventional manner to retrieve the signal data from the waveform D through the data acquisition system 14 via link 42 and is coupled to a suitable display and printer (not shown) for displaying the output information of a sample introduced into the system for analysis through conduit 12. The data acquisition clock 26 may provide clock pulses from about 50 MHz to about 1500 MHz. The data acquisition system 14 includes conventional logic circuits to provide the trigger signals shown by waveform A to the SDS unit 10 as well as the clock pulses C to synchronize the modulator valve control circuit 24 output signals B. Circuit 14 amplifies and digitizes the analog signals D to provide synchronized digital signals to the PC 40 via link 42, which eliminates sampling uncertainty and improves the accuracy of the system.

Figure 2:
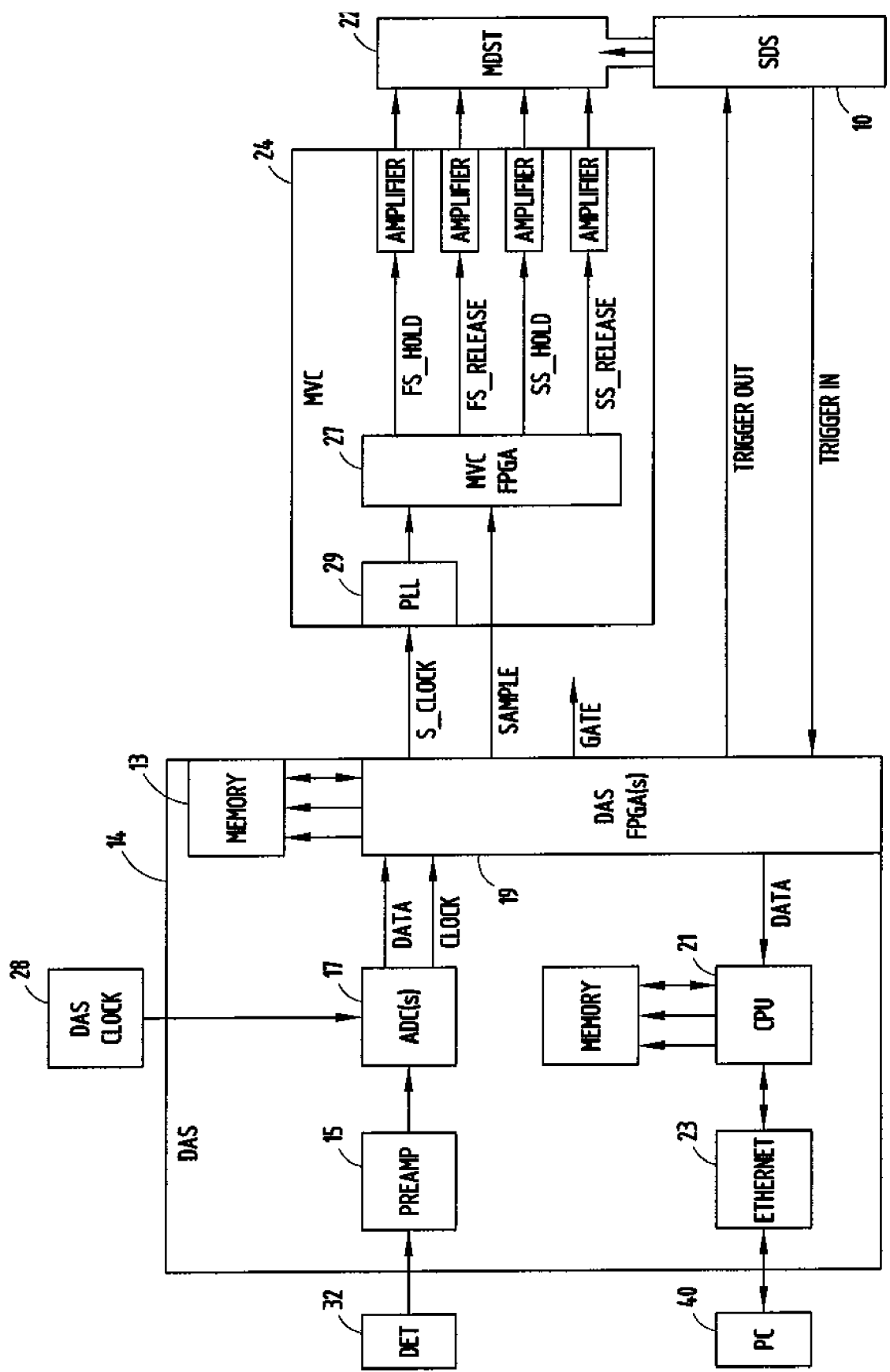
FIG. 2 is a detailed block electrical circuit diagram of the DAS and MVC circuits of FIG. 1.

The FIG. 2 circuit diagram provides additional details about the system. The DAS 14 will amplify the detector output signal with the PREAMP 15, the output of which is sent to multiple analog-to-digital converters (ADCs) 17 to extend the dynamic range of the system. High speed ADCs are typically limited to 8-bits of dynamic range. The clock for the ADCs is driven by the DAS CLOCK 28, The DAS CLOCK is also used to control the sampling interval for the ADCs and the ADCs drive CLOCK and DATA to the DAS field programmable gate arrays (FPGAs) 19 coupled to memory circuit 13. The ADC CLOCK is derived from the DAS CLOCK and is therefore synchronous with the DAS CLOCK. The DAS FPGAs 19 process the data generated by the ADCs to improve the signal to noise ratio and filter the data so that only the relevant information is passed back to the PC 40. The CPU 21 is used to transfer the data from the DAS FPGAs to the PC via an Ethernet circuit 23.

The DAS FPGAs 19 also generate an S_CLOCK signal which is derived from the ADC CLOCK output and is therefore synchronous with the DAS CLOCK. The DAS FPGAs will also generate the SAMPLE and GATE signals for every transient of the TOF/MS 30. The GATE signal is used to control a high voltage pulser that launches a packet of ions into the TOF/MS. The MVC 24 will use the SAMPLE signal to count the how many transients have occurred and after a programmed number of transients it cycles the MDST 22. The number of transients that the MVC will wait before cycling the MDST will match the number of transients for which the DAS FPGAs accumulate the ADC data. The cycle rate of the MDST will therefore match the summation rate of the DAS.

The PLL 29 in the MVC will generate a local clock signal for the MVC FPGA that is synchronous with the S_CLOCK. This will prevent the control signals for the MDST from wandering or drifting with respect to the DAS CLOCK. The MVC FPGA will generate at least four control signals for controlling the MDST which will control how the MDST samples the output of the of the SDS.

The DAS can control the TRIGGER OUT and can respond to the TRIGGER IN. If the system is configured for the DAS to trigger the SDS then the DAS will assert the TRIGGER OUT output. This will cause the DAS and the SDS to start synchronously. If the system is configured such that the SDS will trigger the DAS then the SDS will assert the TRIGGER IN signal. This too will cause the SDS and DAS to start synchronously.

Figure 3:
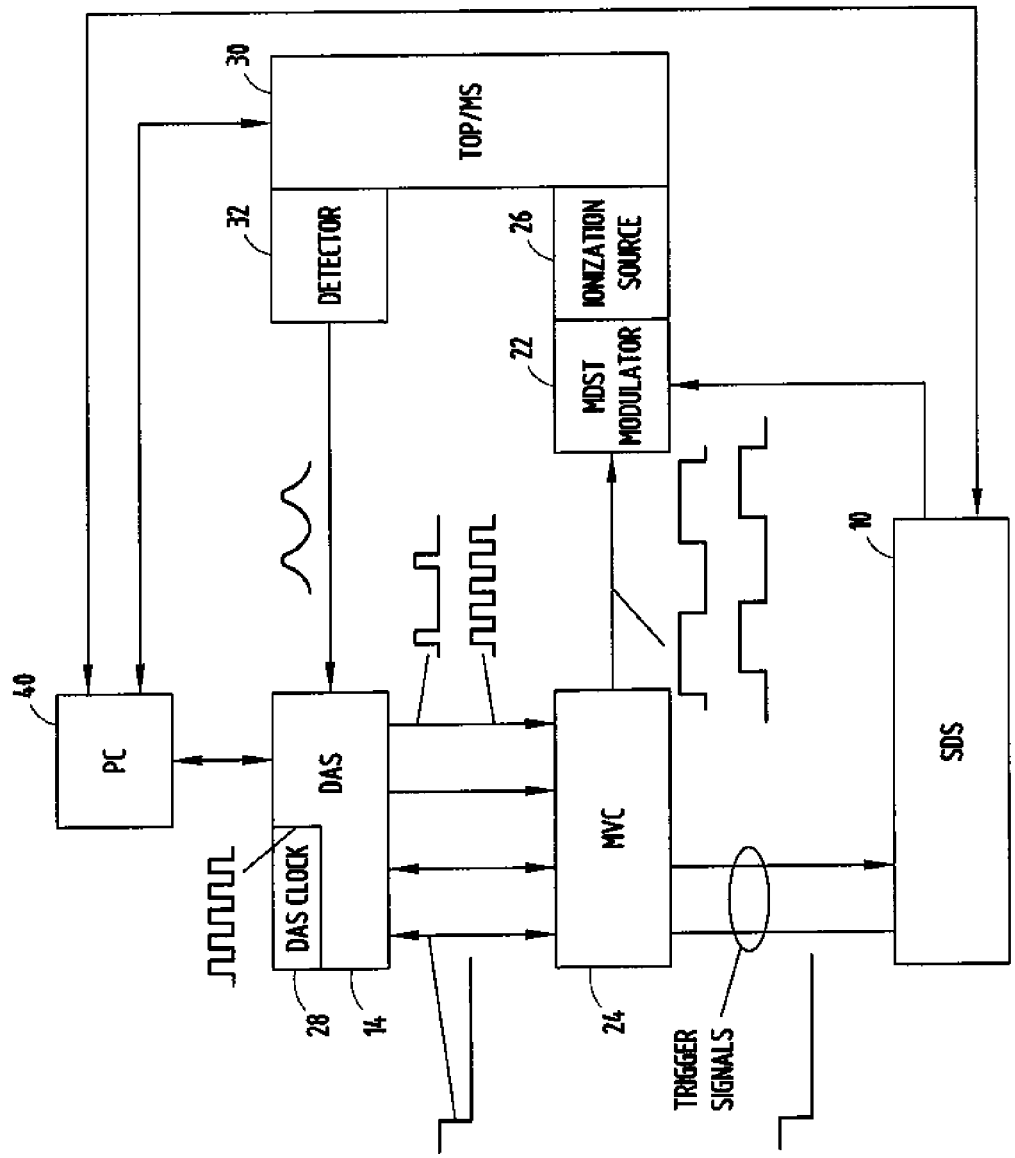
FIG. 3 is a block electrical circuit of an alternative embodiment of the invention.

In the alternate implementation of FIG. 3, the MVC 24 in addition to providing the control for the MDST 22 also provides the interface to the SDS 10. This allows the DAS 14 to be isolated from the details of the SDS. Since the DAS is a complex system, it is difficult to adapt to various SDS systems. The MVC 24 is much easier to modify to allow interfacing to various SDS systems. This system also shows the DAS CLOCK 28 as an integral part of the DAS 14. Since this is a high frequency clock source ($\geq 1.5$ GHz), it will need to reside in the DAS to maintain signal integrity.

Figure 4:
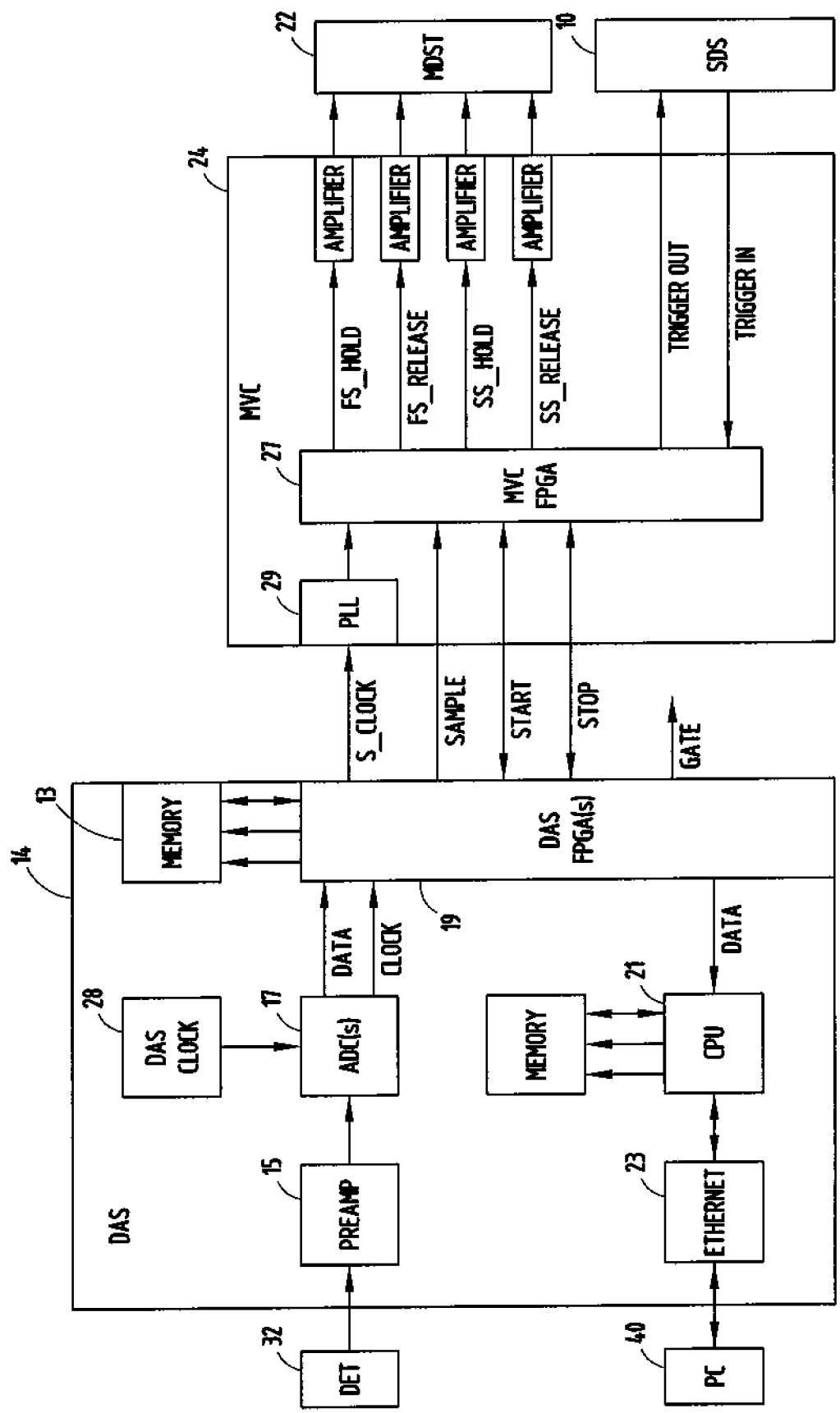
FIG. 4 is a block electrical circuit diagram showing further embodiments of the DAS and MVC circuits.

The FIG. 4 circuit diagram provides additional details on the DAS 14 and the MVC 24. The DAS will amplify the output signal from detector 32 with the PREAMP 15, the output of which is sent to multiple ADCs 17 to extend the dynamic range of the system. High speed ADCs are typically limited to 8-bits of dynamic range. The clock for the ADCs is driven by the DAS CLOCK 28. The DAS CLOCK is used to control the sampling interval for the ADCs and the ADCs drive CLOCK and DATA to the DAS FPGAs 19. The ADC CLOCK is derived from the DAS CLOCK 28 and is, therefore, synchronous with the DAS CLOCK. The DAS FPGAs process the data generated by the ADCs to improve the signal to noise ratio and filter the data so that only the relevant information is passed back to the PC 40. The CPU 21 is used to transfer the data from the DAS FPGAs to the PC 40 through Ethernet 23.

The DAS FPGAs also generate the S_CLOCK which is derived from the ADC CLOCK output and is, therefore, synchronous with the DAS CLOCK. The DAS FPGAs will also generate the SAMPLE and GATE signals every transient of the TOF/MS. The GATE signal is used to control a high voltage pulser that launches a packet of ions into the TOF/MS 30. The MVC will use the SAMPLE signal to count the how many transients have occurred and after a programmed number of transients it cycles the MDST 22. The number of transients that the MVC 24 will wait before cycling the MDST 22 will match the number of transients for which the DAS FPGAs accumulate the ADC data. The cycle rate of the MDST will, therefore, match the summation rate of the DAS.

The PLL 29 in the MVC 24 will generate a local clock for the MVC FPGA that is synchronous with the S_CLOCK. This will prevent the control signals for the MDST 22 from wandering or drifting with respect to the DAS CLOCK. The MVC FPGA 27 will generate at least four control signals for controlling the MDST which will control how the MDST samples the output of the of the SDS 10.

The DAS can control the TRIGGER OUT via the bi-directional START and STOP signals and the MVC can respond to the TRIGGER IN by controlling the START and STOP signals. If the system is configured for the DAS to trigger the SDS, then the DAS will assert the START signal which will cause the MVC to assert the TRIGGER OUT output. This will cause the DAS and the SDS to start synchronously. If the system is configured such that the SDS will trigger the DAS then the SDS will assert the TRIGGER IN which will cause the MVC to assert the START signal. This too will cause the SDS and DAS to start synchronously.

Figure 5:
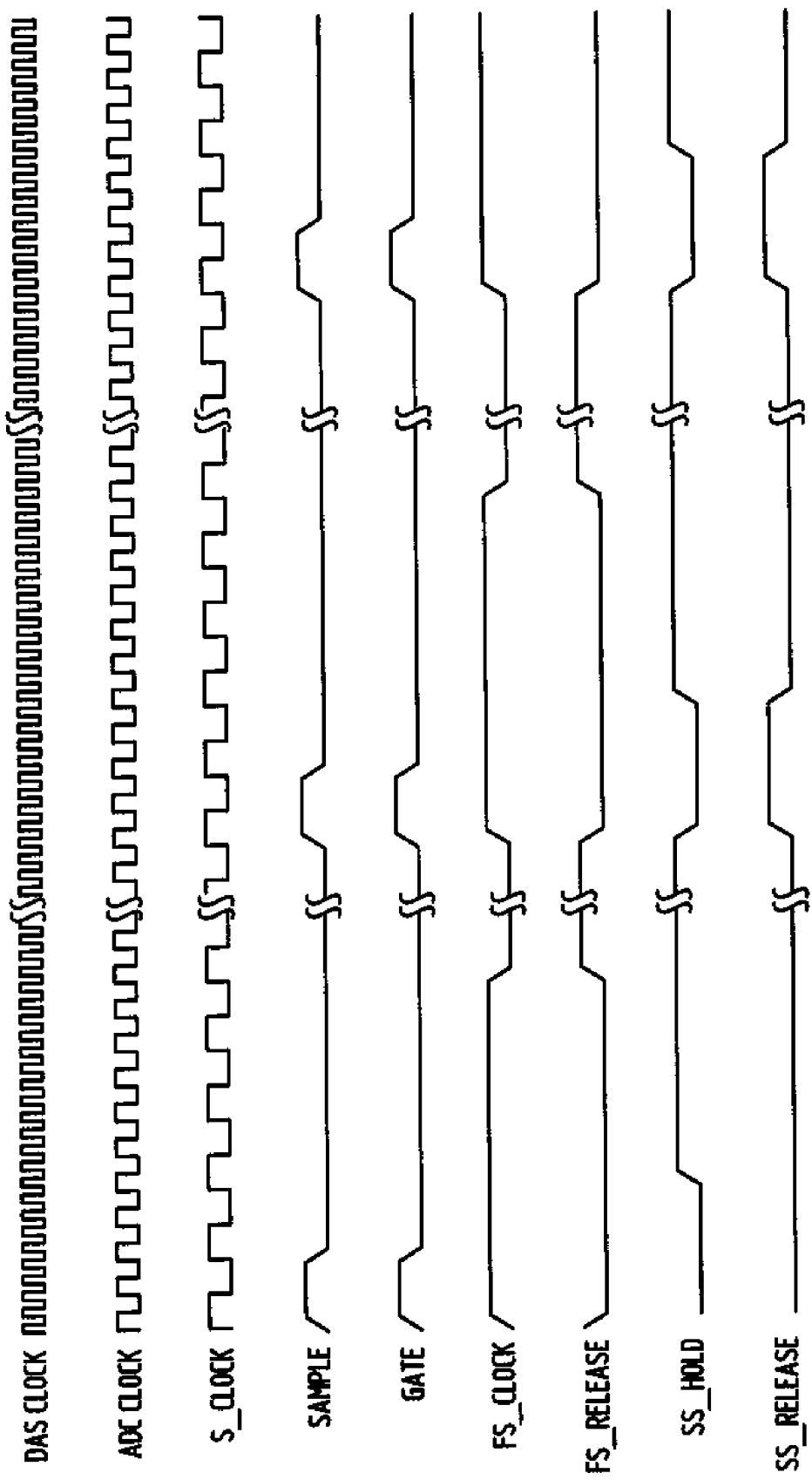
FIG. 5 is a timing diagram showing the relationship between the various timing and control signals.

The timing diagram of FIG. 5 shows the timing relationship between the DAS CLOCK, ADC CLOCK, S_CLOCK, SAMPLE, GATE and MDST control signals. In FIG. 5, the DAS CLOCK is 1.5 GHz, the ADC CLOCK is 750 MHz, the S_CLOCK is 12.5 MHz and the SAMPLE signal has a period of 500 uS to 2 mS. The number of SAMPLE periods (transients) between cycled of the MDST is in the range of 5 to 512.

It will become apparent to those skilled in the art that various modifications to the preferred embodiment of the invention as described herein can be made without departing from the spirit or scope of the invention as defined by the appended claims.

The invention claimed is:

1. A synchronous acquisition system for a multi-dimensional orthogonal liquid separation system comprising:
   a liquid sample inlet;
   a first liquid separating column including controlled valves;
   a data acquisition clock providing clock output signals;
   a data acquisition circuit coupled to said clock for receiving clock pulses therefrom and for providing controlled output signals synchronized with said clock pulses to said controlled valves of said first column;
   a modulator valve control circuit coupled to said data acquisition system for receiving clock pulses and control signals therefrom;
   a multi-dimensional separation modulator coupled to said modulator valve control circuit for receiving synchronized valve control pulses therefrom;
   a second liquid separating column coupled to said multi-dimensional separation modulator for receiving time synchronized pulses of liquid samples; and
   a detection circuit coupled to said second liquid separating column for providing data output signals to said data acquisition circuit which are read in synchronous relationship to the liquid sample peaks from said second liquid separating column.

2. The system as defined in claim 1 and further including a computer coupled to said data acquisition circuit for receiving and processing signal information therefrom.

3. The system as defined in claim 1 wherein said detection circuit includes an ionization source coupled to said second liquid separating column, a TOF/MS coupled to said ionization source, and a detector for detecting ions separated by said TOF/MS to provide said data output signals.

4. The system as defined in claim 1 wherein said data acquisition circuit includes a plurality of field programmable gate arrays.

5. The system as defined in claim 4 wherein said data acquisition circuit further includes a plurality of analog-to-digital converters.

6. The system as defined in claim 5 and further including a computer coupled to said data acquisition circuit for receiving and processing signal information therefrom.

7. The system as defined in claim 6 wherein said detection circuit includes an ionization source coupled to said second liquid separating column, a TOF/MS coupled to said ionization source, and a detector for detecting ions separated by said TOF/MS to provide said data output signals.

8. A time-of-flight mass spectrometer including a synchronous data acquisition system for a multi-dimensional orthogonal liquid separation system comprising:
   a liquid sample inlet;
   a first liquid separating column including controlled valves;
   a data acquisition clock providing clock output signals;
   a data acquisition circuit coupled to said clock for receiving clock pulses therefrom and for providing controlled output signals synchronized with said clock pulses to said controlled valves of said first column;
   a modulator valve control circuit coupled to said data acquisition system for receiving clock pulses and control signals therefrom;
   a multi-dimensional separation modulator coupled to said modulator valve control circuit for receiving synchronized valve control pulses therefrom;
   a second liquid separating column coupled to said multi-dimensional separation modulator for receiving time synchronized pulses of liquid samples;
   a detection circuit coupled to said second liquid separating column for providing data output signals to said data acquisition circuit which are read in synchronous relationship to the liquid sample peaks from said second liquid separating column;
   an ionization source coupled to said second liquid separating column; and
   a TOF/MS coupled to said ionization source and a detector for detecting ions separated by said TOF/MS to provide said data output signals.

9. The system as defined in claim 8 and further including a computer coupled to said data acquisition circuit for receiving and processing signal information therefrom.

10. The system as defined in claim 9 wherein said data acquisition circuit includes a plurality of field programmable gate arrays.

11. The system as defined in claim 10 wherein said data acquisition circuit further includes a plurality of analog-to-digital converters.

12. The system as defined in claim 11 and further including a computer coupled to said data acquisition circuit for receiving and processing signal information therefrom.

13. The system as defined in claim 12 wherein said detection circuit includes an ionization source coupled to said second liquid separating column, a TOF/MS coupled to said ionization source, and a detector for detecting ions separated by said TOF/MS to provide said data output signals.

14. A synchronous data acquisition system for a multi-dimensional orthogonal liquid separation system comprising:
   a liquid sample inlet;
   a first liquid separating column including a plurality of controlled valves;
   a data acquisition clock providing clock output signals;
   a data acquisition circuit coupled to said data acquisition clock for receiving clock pulses therefrom and for providing control output signals synchronized with said clock pulses to said controlled valves of said first column;
   a modulator valve control circuit coupled to said data acquisition system for receiving clock pulses and said control signals therefrom;
   a multi-dimensional separation modulator coupled to said modulator valve control circuit for receiving synchronized valve control pulses therefrom;
   a delay loop coupled to said first liquid separating column;
   a second liquid separating column coupled to said delay loop and to said multi-dimensional separation modulator for receiving time synchronized pulses of liquid samples; and
   a detection circuit coupled to said second liquid separating column for providing data output signals to said data acquisition circuit which are read in synchronous relationship to the liquid sample peaks from said second liquid separating column.

15. The system as defined in claim 14 and further including a computer coupled to said data acquisition circuit for receiving and processing signal information therefrom.

16. The system as defined in claim 15 wherein said detection circuit includes an ionization source coupled to said second liquid separating column, a TOF/MS coupled to said ionization source, and a detector for detecting ions separated by said TOF/MS to provide said data output signals.

17. The system as defined in claim 16 wherein said data acquisition circuit includes a plurality of field programmable gate arrays.

18. The system as defined in claim 17 wherein said data acquisition circuit further includes a plurality of analog-to-digital converters.

19. The system as defined in claim 18 and further including a computer coupled to said data acquisition circuit for receiving and processing signal information therefrom.

20. The system as defined in claim 19 wherein said detection circuit includes an ionization source coupled to said second liquid separating column, a TOF/MS coupled to said ionization source and a detector for detecting ions separated by said TOF/MS to provide said data output signals.

* * * * *